United States Patent
Margolis et al.

(10) Patent No.: US 7,627,156 B2
(45) Date of Patent: Dec. 1, 2009

(54) AUTOMATED LESION ANALYSIS BASED UPON AUTOMATIC PLAQUE CHARACTERIZATION ACCORDING TO A CLASSIFICATION CRITERION

(75) Inventors: Marja Pauliina Margolis, Coral Gables, FL (US); D. Geoffrey Vince, Avon Lake, OH (US); Anuja Nair, Copley, OH (US); Vincent J. Burgess, San Diego, CA (US)

(73) Assignee: Volcano Corporation, Rancho Cordova, CA (US)

( * ) Notice: Subject to any disclaimer, the term of this patent is extended or adjusted under 35 U.S.C. 154(b) by 0 days.

(21) Appl. No.: 11/689,963

(22) Filed: Mar. 22, 2007

(65) Prior Publication Data

US 2007/0260141 A1 Nov. 8, 2007

Related U.S. Application Data

(60) Provisional application No. 60/785,267, filed on Mar. 22, 2006, provisional application No. 60/797,333, filed on May 2, 2006, provisional application No. 60/844,977, filed on Sep. 15, 2006.

(51) Int. Cl.
*G06K 9/00* (2006.01)
*A61B 5/05* (2006.01)

(52) U.S. Cl. .......................... 382/128; 382/224; 600/427

(58) Field of Classification Search ................. 382/100, 382/128, 129, 130, 131, 132, 133, 134, 168, 382/170, 173, 191, 194, 199, 203, 224, 232, 382/258, 274, 276, 285, 291, 305, 312; 600/443, 600/549, 478, 427; 606/15; 607/15

See application file for complete search history.

(56) References Cited

U.S. PATENT DOCUMENTS

| | | | | |
|---|---|---|---|---|
| 4,063,549 A | * | 12/1977 | Beretsky et al. | 600/443 |
| 6,450,971 B1 | * | 9/2002 | Andrus et al. | 600/549 |
| 6,564,088 B1 | * | 5/2003 | Soller et al. | 600/478 |
| 6,712,771 B2 | * | 3/2004 | Haddock et al. | 600/549 |
| 7,153,299 B1 | * | 12/2006 | Tu et al. | 606/15 |
| 7,297,154 B2 | * | 11/2007 | Tu et al. | 607/88 |
| 7,374,538 B2 | * | 5/2008 | Nightingale et al. | 600/443 |
| 2005/0043614 A1 | * | 2/2005 | Huizenga et al. | 600/427 |

OTHER PUBLICATIONS

Nair, A,; Vince, D.G..; Calvetti,D."Blind, data calibration of intravascular ultrasound data for automated tissue characterization," Ultrasonic Symposium, 2004 IEEE, vol. 2, no., pp. 1126-1129 vol. 2, Aug. 23-27, 2004.*

International Search Report And Written Opinion for PCT/US07/64698 dated Jul. 3, 2008.

* cited by examiner

*Primary Examiner*—Seyed Azarian
(74) *Attorney, Agent, or Firm*—Leydig, Voit & Mayer, Ltd.

(57) ABSTRACT

A system and method are disclosed for automatically classifying plaque lesions. A plaque classification application applies a plaque classification criterion to at least one graphical image, comprising a map of spectrally-analyzed characterized tissue of a vessel cross-section, to render an overall plaque classification for the slice or set of slices, covering a 3D volume. The plaque classification is based upon the amount and location of each characterized tissue type (e.g., necrotic core—NC). In an exemplary embodiment the set of potential plaque classifications, not to be confused with characterized tissue types—from which the plaque classifications are derived—include, for example: adaptive intimal thickening (AIT), pathological intimal thickening (PIT), fibroatheroma (FA), thin-cap fibroatheroma (TCFA), and fibro-calcific (FC).

24 Claims, 2 Drawing Sheets

| | |
|---|---|
| AIT | Adaptive Intimal Thickening |
| PIT | Pathological Intimal Thickening |
| FA | Fibro-Atheroma |
| TCFA | Thin Cap Fibro-Atheroma |
| CaTCFA | Calcified Thin Cap Fibro-Atheroma |
| Ca FA | Calcified Fibro-Atheroma |
| FT | Fibrous Plaque |
| FC | Fibro Calcific |

AUTOMATED LESION ANALYSIS BASED UPON AUTOMATIC PLAQUE CHARACTERIZATION ACCORDING TO A CLASSIFICATION CRITERION

CROSS-REFERENCE TO RELATED APPLICATION

This application claims priority of Margolis et al. U.S. provisional application Ser. No. 60/785,267 filed on Mar. 22, 2006, entitled "Lesion Analysis Automatic Plaque Classification," and Margolis et al. U.S. provisional application Ser. No. 60/797,333 filed on May 2, 2006, entitled "Lesion Analysis Rules," the contents of both of the above-identified provisional applications are expressly incorporated herein by reference in their entirety including the contents and teachings of any references contained therein.

This application claims priority of Margolis et al., U.S. provisional application Ser. No. 60/844,977 filed on Sep. 15, 2006, entitled "Guidelines For Virtual Histology Intravascular Ultrasound Based Lesion Analysis."

FIELD OF THE INVENTION

The present invention generally relates to the field of imaging systems, and more particularly to intravascular imaging systems used to diagnose and treat vascular disease.

BACKGROUND OF THE INVENTION

The development of new medical technologies has provided an increasing number of options available to doctors for the diagnosis and treatment of cardiovascular diseases. The availability of such equipment has improved the ability of doctors and surgeons to detect and treat cardiovascular disease. Intravascular imaging technologies have enabled doctors to create and view a variety of images generated by a sensor inserted within a vasculature. Such images compliment traditional radiological imaging techniques such as angiography by providing images of the tissue within vessel walls rather than showing a two dimensional lumen image.

Intravascular ultrasound (IVUS) analysis finds particular application to a system and method for quantitative component identification within a vascular object including characterization of tissue. It should be appreciated that while the exemplary embodiment is described in terms of an ultrasonic device, or more particularly the use of IVUS data (or a transformation thereof) to characterize a vascular object, the present invention is not so limited. Thus, for example, using backscattered data (or a transformation thereof) based on ultrasound waves or even electromagnetic radiation (e.g., light waves in non-visible ranges) to classify tissue according to a type or composition is within the spirit and scope of the present invention.

Imaging portions of a patient's body provides a useful tool in various areas of medical practice for determining the best type and course of treatment. Imaging of the coronary vessels of a patient by techniques involving insertion of a catheter-mounted probe (e.g., an ultrasound transducer array) can provide physicians with valuable information. For example, the image data indicates the extent of a stenosis in a patient, reveals progression of disease, helps determine whether procedures such as angioplasty or atherectomy are indicated or whether more invasive procedures are warranted.

In an ultrasound imaging system, an ultrasonic transducer probe is attached to a distal end of a catheter that is carefully maneuvered through a patient's body to a point of interest such as within a coronary artery. The transducer probe in known systems comprises a single piezoelectric crystal element that is mechanically scanned or rotated back and forth to cover a sector over a selected angular range. Acoustic signals are transmitted and echoes (or backscatter) from these acoustic signals are received. The backscatter data is used to identify the type or density of a scanned tissue. As the probe is swept through the sector, many acoustic lines are processed building up a sector-shaped image of the patient. After the data is collected, an image of the blood vessel (i.e., an IVUS image) is reconstructed using well-known techniques. This image is then visually analyzed by a cardiologist to assess the vessel components and plaque content. Other known systems acquire ultrasound echo data using a probe comprising an array of transducer elements.

In a particular application of IVUS imaging, ultrasound data is used to characterize tissue within a vasculature and produce images graphically depicting the content of the tissue making up imaged portions of a vessel. Examples of such imaging techniques based on spectral analysis of ultrasound backscatter data and color-coded tissue maps are presented in Nair et al. U.S. Pat. No. 7,074,188 entitled "System and Method of Characterizing Vascular Tissue" and Vince et al. U.S. Pat. No. 6,200,268 entitled "Vascular Plaque Characterization", the contents of which are incorporated herein by reference in their entirety, including any references contained therein. Such systems analyze response characteristics of ultrasound backscattered (reflected sound wave) data to identify a variety of tissue types (also referred to as "plaque components") found in vessel occlusions including: fibrous tissue (FT), fibro-fatty (FF), necrotic core (NC), and dense calcium (DC).

When characterizing the response of tissue when exposed to ultrasound waves, parameter values are considered at a data point in an imaged field. Based upon response characteristics of known tissue types, tissue at the data point is assigned to a particular tissue type (e.g. necrotic core). The set of character data points in an imaged field are thereafter converted into viewable cross-sectional image wherein the various identified types of tissue are presented in a color-coded form for clinical analysis. In a particular known system, the detected area of a cross-sectional "slice" of an imaged vessel occupied by each tissue type is calculated. For example, upon completing a tissue characterization analysis, the system renders cross-sectional areas occupied by dense calcium, fibrous, fibro-fatty, and necrotic core tissue. Furthermore, the compositional information generated at each cross-sectional slice during a pull-back procedure is stored as a series of data sets, and the composition of the various plaque classes at each slice is graphically represented two-dimensionally as plaque composition (area) at each slice covering a series of sequential blood vessel cross-sections.

While the known tissue characterization systems provide visually discernable features, the importance of each type of plaque tissue, including its overall amount, confluency, and position in the cross-section is subject to the personal experience and training of each viewer. Thus, two individuals viewing a same cross-sectional image potentially come to significantly different diagnoses and proposed courses of treatment.

SUMMARY OF THE INVENTION

In accordance with the present invention a system and method are provided for automatically classifying plaque lesions wherein a classification criterion is applied by a plaque classification application to at least one graphical image of a cross-sectional slice of a vessel to render an overall plaque classification for the slice or set of slices, covering a 3D volume. Thus, in alternative embodiments a three-dimensional analysis is performed wherein a lesion type is rendered from tissue type information processed over multiple sequential vessel cross-sections.

The plaque classification is based upon the amount and location of each characterized tissue type (e.g., necrotic core—NC). In an exemplary embodiment the set of potential plaque classifications, not to be confused with characterized tissue types—from which the plaque classifications are derived—include, for example: adaptive intimal thickening (AIT), pathological intimal thickening (PIT), fibroatheroma (FA), thin-cap fibroatheroma (TCFA), and fibro-calcific (FC). Each of these types of plaque types is described in the specification herein below.

BRIEF DESCRIPTION OF THE DRAWINGS

While the claims set forth the features of the present invention with particularity, the invention, together with its objects and advantages, may be best understood from the following detailed description taken in conjunction with the accompanying drawing of which:

DETAILED DESCRIPTION OF THE DRAWINGS

The disclosed system and method for classifying plaque/lesions in blood vessels apply a classification criterion to a tissue characterization image for at least one blood vessel cross-section. The characterization image is, for example, a colorized tissue map image rendered from frequency response parameters associated with an IVUS probe's field of view including a blood vessel's cross-section. The classification criterion supports automatic identification of plaque/lesion types (e.g., adaptive intimal thickening (AIT), pathological intimal thickening (PIT), fibroatheroma (FA), thin-cap fibroatheroma (TCFA), and fibro-calcific (FC)) based upon the amount and location of characterized tissue (e.g., fibrous tissue (FT), fibro fatty (FF), necrotic core (NC), and dense calcium (DC)). The aforementioned lesion types are well recognized by medical standards organizations.

The classification criterion facilitates identifying potential vulnerable plaque events (e.g., TCFA), as well as the location of the particular plaque type in a vessel cross-section. By way of example, a more proximal location of a lesion in a major vessel likely poses a greater risk to a patient. In exemplary embodiments, the analysis of cross-sectional tissue characterization images occurs in real time while the patient is on the procedural table. A physician is provided the opportunity to take immediate interventional actions to address a significant health threat identified by the automated plaque classification procedure. Examples of such intervention include positioning a particular drug eluting stent within a diseased artery—as opposed to delaying analysis of the tissue image information and needed treatment for the patient.

The plaque classification criterion, in an illustrative embodiment, identifies lesions comprising multiple layers of fibro-atheromas. Such lesions represent likely sites of previous plaque ruptures. Such identification is potentially performed in association with gray scale IVUS images generated from ultrasound echo intensity information at a same location in a vessel since the layering is generally better depicted in the gray scale images. In combination, the gray scale images and confirmation via the plaque classification criterion improve identification of such lesions In accordance with an exemplary embodiment, a vulnerability index includes a ranking of patient risk associated with identified plaque classifications. Yet other embodiments refine the vulnerability index based upon patient information/factors including, for example, diabetes or hypertension.

An exemplary IVUS (intravascular ultrasound) system includes an ultrasonic probe device mounted upon a flexible elongate member for insertion into a vasculature. The system furthermore includes a computing device comprising memory for storing computer executable instructions associated with a plaque classification application program.

Figures 1, 2:
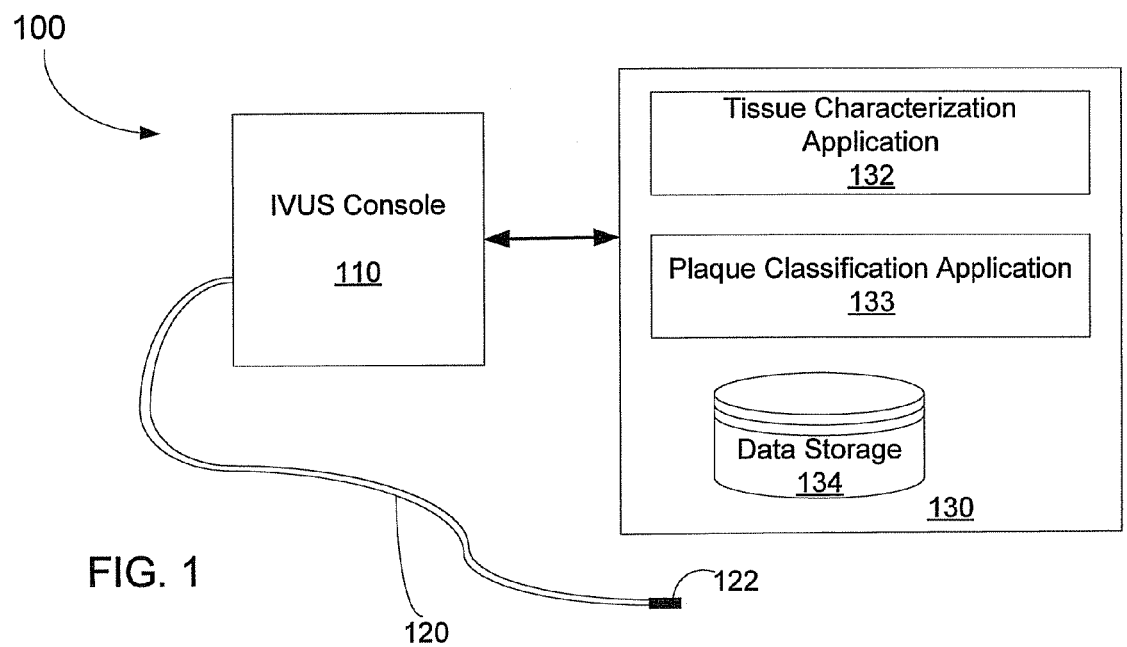
FIG. 1 illustrates a tissue-characterization system suitable for carrying out the disclosed tissue/plaque characterization scheme including multiple characterization criteria applied to multiple ranges of tissue/plaque depth associated with IVUS echo information.
FIG. 2 is a table identifying a set of plaque classifications that are identifiable using an automated plaque classification method and system that renders a plaque type from characterized tissue data over a blood vessel cross-section.

Turning initially to FIG. 1, a plaque classification system 100 is schematically depicted. An intravascular ultrasound console 110 is communicatively coupled to an IVUS catheter 120. The IVUS catheter 120 comprises a distally mounted ultrasound transducer probe 122 that acquires backscatter data (i.e., IVUS data) from a blood vessel. In accordance with known IVUS catheters, the catheter 120 is maneuvered through a patient's body (e.g., via a femoral artery) to a point of interest. The transducer probe 122 is then controlled, via the console 110 to emit ultrasound pulses and thereafter receive echoes or backscattered signals reflected from vascular tissue/plaque and blood. Because different types and densities of tissue absorb and reflect the ultrasound pulse differently, the reflected data (i.e., IVUS data) signals transmitted back to the console 110 by the IVUS catheter 120, is converted by software for performing analysis on ultrasound echoes to render tissue maps of vascular objects. It should be appreciated that the IVUS console 110 depicted herein is not limited to any particular type of IVUS console, and includes all ultrasonic devices known to those skilled in the art (e.g., InVision and s5 systems of Volcano Corporation). It should further be appreciated that the IVUS catheter 120 depicted herein is not limited to any particular type of catheter, and includes all ultrasonic catheters known to those skilled in the art. Thus, for example, a catheter having a single transducer (e.g., adapted for rotation) or an array of transducers (e.g., circumferentially positioned around the catheter) is within the spirit and scope of the present invention.

Known imaging applications executed on an IVUS console (e.g. console 110) or a communicatively coupled computing device (e.g., computing device 130), render a variety of image types from received echo information. A first type of imaging application converts ultrasound echo signal data into gray scale images reflecting the relative strength of the echo signal returned by the objects within the transducer probe 120's field of view. In such imaging applications, the relatively light and dark regions indicate different tissue types and/or densities.

Other imaging applications, such as a tissue characterization application 132 executed on the computing device 130 communicatively coupled to console 110, render a color-coded characterized tissue map of vascular objects based upon the spectral characteristics of the echo information received by the console 110 from the catheter 120. The spectral information extracted from the echo information rendered by the catheter 120, is compared to the frequency response signatures associated with particular types of tissue/plaque to render a tissue/plaque characterization image.

In accordance with an exemplary embodiment, a plaque classification application 133, comprising a set of computer-executable instructions and a plaque classification criterion stored on a computer-readable medium, analyzes the characterized tissue map of vascular objects rendered by the tissue characterization application 132 to render plaque classification data for single vessel cross-sections as well as vessel segments constructed from consecutive cross-sectional vessel slices. The functionality and exemplary logic of the plaque classification application 133 is described further herein below.

A data storage 134 stores the tissue/plaque characterization images/maps rendered by the characterization application 132 from the echo information received from the console 110. The data storage 134 is, by way of example, any of a variety of data storage devices, including RAM, cache memory, flash memory, magnetic disks, optical disks, removable disks, SCSI disks, IDE hard drives, tape drives, optically encoded information discs (e.g., DVD) and all other types of data storage devices (and combinations thereof, such as RAID devices) generally known to those skilled in the art.

In closing with regard to FIG. 1, the number and location of the components depicted in FIG. 1 are not intended to limit the present invention, and are merely provided to illustrate the environment in which an exemplary system operates. Thus, for example, a computing device having a plurality of data storage devices and/or a remotely located characterization application (either in part or in whole) is within the spirit and scope of the present invention.

In accordance with an illustrative embodiment, the plaque classification application 133 applies a pre-programmed/configured criterion to the tissue characterization information/maps for one or more vessel cross-sections provided by the characterization application 132 to render plaque classification decisions regarding vessel tissue cross-sections. Turning to FIG. 2, an exemplary list of plaque classifications and associated abbreviations are provided. Adaptive intimal thickening (AIT) is a type of occlusion that is not quite classified as a plaque since the amount of occlusion is low and not pathological. Pathological intimal thickening (PIT) is a type of plaque comprising primarily a mixture of fibrous and fibro-fatty (greater than 15%), including minimal necrotic core (less than 5%) and calcified tissue (less than 5%).

Fibro-Atheroma (FA) is a plaque form having a thick fibrous cap and significant necrotic core (confluent necrotic core is greater than 5% of the total plaque volume) in fibrous and/or fibro-fatty tissue. FA is sub-divided into sub-classes, based on the amount of dense calcium that is present, including: (1) FA containing a minor amount of DC (less than 5% of plaque volume, and (2) FA with a significant amount of DC (greater than 5%), called Calcified Fibro-Atheroma (Ca FA)—which in turn could be divided into focal or diffuse based on a length of the necrotic core component in the FA.

Yet another plaque classification addressed by a criterion described herein below is Thin Cap Fibro-Atheroma (TCFA). TCFA generally has greater than 10% necrotic core, without evidence of fibrous cap. TCFA could be further divided into four sub-classes according to relative vulnerability/threat level including from lowest to highest vulnerability: (1) TCFA having less than 5% dense calcium; (2) TCFA having greater than 5% dense calcium or Calcified Thin Cap Fibro-Atheroma (Ca TCFA); (3) TCFA having multiple confluent necrotic cores, including at least one necrotic core without evidence of a fibrous cap—suggesting a previous rupture with calcification; and (4) TCFA having greater than 20% necrotic core with no evidence of fibrous cap, dense calcium greater than 5%, and greater than 50% cross-sectional area luminal narrowing (observed via gray scale IVUS image).

Fibro Calcific (FC) plaque is primarily fibrous tissue with greater than 5% dense calcium. FC has less than 5% necrotic core. Single or multiple layers of calcium are present—with or without narrowing—in the form of deep or superficial sheets of calcium. In general, such plaque is potentially stable. Finally, Fibrous plaque (FT) is mainly fibrous in composition and bigger than AIT.

Figure 3:
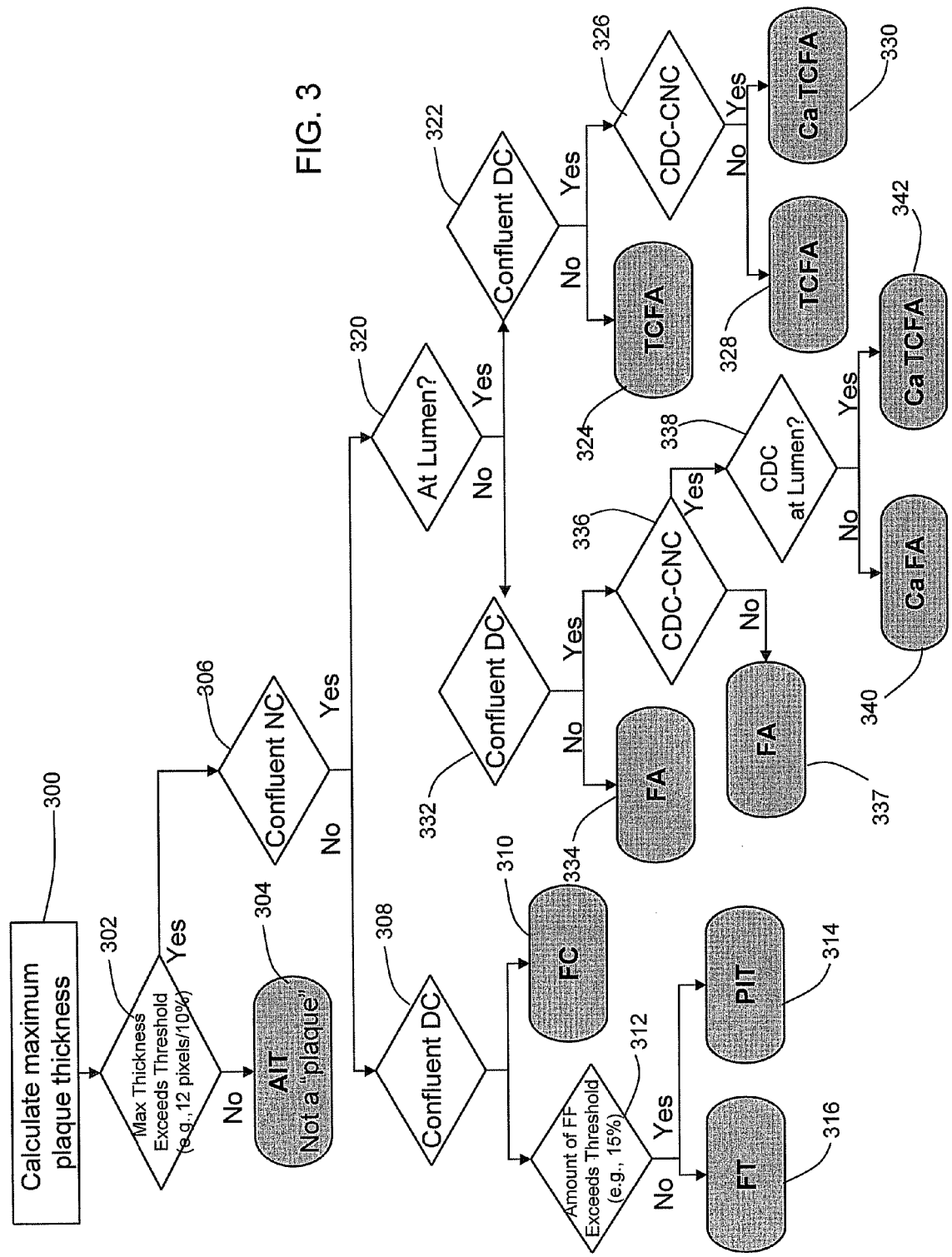
FIG. 3 is a flowchart summarizing an exemplary set of steps for a plaque classification procedure that renders a plaque type based upon an analysis of the amount and location of tissue types in a blood vessel cross-section.

Turning to FIG. 3, a flowchart summarizes an exemplary plaque classification scheme/criterion that is implemented by analyzing a characterized tissue map (e.g., a two-dimensional display of plaque components including: FT, FF, NC, and DC) of vascular objects based upon the spectral characteristics of the echo information received by the console 110 from the catheter 120. In alternative embodiments, the plaque classification scheme/criterion is enhanced to classify plaque based upon volumetric/three-dimensional information provided by multiple adjacent cross-sectional vessel slices.

Initially, during step 300 a spectrally analyzed tissue map (e.g., two-dimensional pixel map) for a vessel cross-section under observation is analyzed to determine a maximum plaque thickness around the vessel's lumen and/or the presence of a stenosis. In the exemplary embodiment, a plaque thickness of 12 pixels (in a 328×328 pixel map), which corresponds to a distance of 400 microns, distinguishes potentially significant plaque lesions and AIT. Therefore, during step 302 if the maximum thickness of plaque is less than 12 pixels (400 microns), then control passes to step 304 and the plaque classification application 133 assigns an AIT class to the vessel cross-section under observation. In addition to measuring the maximum thickness, in an exemplary embodiment, if the plaque thickness of more than 12 pixels/400 microns does not exceed 10 percent of the vessel's circumference, then control passes to step 304 and the AIT class is assigned to the cross-section under observation. If the classification application 133 determines that the plaque thickness exceeds 12 pixels (for at least 10 percent of the vessel's circumference), then control passes from step 302 to step 306 wherein the classification application commences examining the composition and location of different components within the plaque structure to automatically render a plaque classification for the vessel cross-section under observation.

During step 306 the classification application 133 identifies the existence of confluent NC (CNC) tissue within the vessel cross-section. The presence of confluent NC is determined by identifying clusters of pixels identified as NC (e.g., assigned the color red—corresponding to NC tissue) in the tissue characterization tissue map of the vessel cross-section.

If, at step 306, confluent NC is not identified, then control passes to step 308 wherein the classification application 133 identifies confluent DC (CDC) within the vessel cross-section image. At step 308 clusters of DC pixels are analyzed according to a threshold measure for confluent DC. If a significant portion of the vessel cross-section is confluent DC, then control passes to step 310 wherein the classification application 133 assigns an FC class to the vessel cross-section.

Otherwise, if confluent DC is not observed during step 308, then control passes to step 312 wherein the classification application 133 calculates the percentage of fibro fatty (FF) tissue in the plaque depicted in the pixel image of the vessel cross-section. If a significant percentage (e.g., greater than 15 percent) of the plaque is FF tissue, then control passes to step 314 wherein the plaque classification application assigns a pathological intimal thickening (PIT) class to the vessel cross-section. Alternatively, if the FF tissue percentage does not exceed the established threshold (e.g., 15 percent), then control passes from step 312 to step 316 wherein a fibrous plaque (FT) class is assigned.

Returning to step 306 if confluent NC is identified by the plaque classification application 133, then control passes to step 320. During step 320 the classification application 133 determines whether confluent NC is present at the lumen-plaque border. If confluent NC is indeed present at the lumen-plaque border, then the plaque is TCFA and control passes to step 322 to determine the degree of threat posed by the TCFA plaque.

During step 322 if confluent DC is not present, then control passes to step 324 and a TCFA classification is assigned to the cross-section. The TCFA classification identifies a first level of high risk for vulnerable plaque. Otherwise, if confluent DC is identified during step 322, then control passes to step 326 wherein the classification application 133 searches the cross-sectional image for confluent DC attached to confluent NC. By way of example, "attached to" is defined to exist when any pixel of confluent DC is adjacent to any pixel of confluent NC. If such attachment is not identified, then control passes from step 326 to step 328 wherein the classification application 133 assigns the TCFA class to the vessel cross-section. Otherwise, if attachment is identified, then control passes from step 326 to step 330 wherein a Ca TCFA class is assigned. The Ca TCFA class is considered to be a higher risk plaque lesion than a TCFA class.

Returning to step 320, if confluent NC is not located at the lumen, then control passes to step 332. At step 332 the classification application analyzes the cross-sectional tissue map image for confluent DC. If confluent DC is not present, then control passes from step 332 to step 334 wherein the vessel cross-section is assigned a fibro-atheroma (FA) classification. If, however, confluent DC is identified, then control passes from step 332 to step 336.

At step 336 the classification application 133 searches the cross-sectional tissue map for confluent DC attached to confluent NC. If no attachment is observed, then control passes to step 337 wherein the FA classification is assigned to the vessel cross-section. However, if attachment is observed between confluent DC and confluent NC plaque components, then control passes from step 336 to step 338.

During step 338 the classification application 133 searches the tissue map image for the presence of confluent DC at the lumen-plaque border. If confluent DC is not present at the lumen-plaque border, then control passes to step 340 wherein the classification application 133 assigns a calcified fibro-atheroma (Ca FA) class to the vessel cross-section. If confluent DC is detected at the lumen-plaque border, then control passes to step 342 and the calcified thin cap fibro-atheroma (Ca TCFA) class is assigned to the cross-section to indicate to an observer/reviewer of the classification application 133's output that a relatively high risk lesion is present at the corresponding vessel cross-section.

An aspect of the automated nature of the plaque classification application 133 is that it will render a positive class identification for each vessel cross-section (or alternatively a sequence of adjacent slices making up a vessel segment). Thus, there are no "unknown" classes for vessel cross-sections. In yet other embodiments, in addition to assigning a plaque classification, the plaque classification application 133 stores key parameter values that led to the plaque classification.

Yet another feature of an illustrative embodiment of the automated plaque classification application 133 is assignment of a code, such as a color, to each slice based upon the vulnerability/threat posed by the plaque in any given cross-section or vessel segment. The slices/segments are in turn graphically displayed in a manner that visually represents the threat level. For example, the assigned value for vessel segments are merged with a two or three-dimensional rendering of a blood vessel segment. Values/colors assigned to the various segments are visually rendered to indicate both the severity of a threat posed by vulnerable plaque and the location of the plaque within the vessel segment.

It is noted that the above described example of a plaque/lesion classification scheme is exemplary and not intended to limit the scope of the present invention. As more tissue component composition classes (not necessarily limited to plaque components) are identified, new classification applications/criteria are developed to aid the standardization of identification of particular tissue compositions imaged from backscattered signals. Furthermore the thresholds for confluent tissue types, attachment, and location at the lumen surface are subject to a variety of potentially complete decision processes. However, in the various embodiments, the classification application 133's automatic application of a criterion ensures timely (e.g., near real-time) consistent/objective analysis of plaque lesions to identify various levels of threat/vulnerability posed by identified plaque within a vessel.

Systems and their associated components have been described herein above with reference to exemplary embodiments of the invention including their structures and techniques. In view of the many possible embodiments to which the principles of this invention may be applied, it should be recognized that the embodiments described herein with respect to the drawing figures are meant to be illustrative only and should not be taken as limiting the scope of invention. Therefore, the invention as described herein contemplates all such embodiments as may come within the scope of the following claims and equivalents thereof.

What is claimed is:

1. A method of classifying plaque within a vessel, comprising:
   rendering, by a tissue characterization application, a characterized tissue component map from a spectral analysis of ultrasound echo information for a vessel cross-section, wherein differing plaque components are distinguished, in the characterized tissue map, by assigned identifying values;
   applying, by a plaque classification application, a classification criterion to spatially arranged data of the characterized tissue map, wherein the classification criterion includes a rule based upon a location, in relation to a lumen-plaque border, of confluent necrotic core within the vessel cross-section; and
   rendering, in response to the applying step, a plaque classification associated with the vessel cross-section.

2. The method of claim 1 wherein the classification criterion renders a plaque classification for each vessel cross-section.

3. The method of claim 1 wherein the plaque classification application applies a set of hierarchically arranged classification rules.

4. The method of claim 3 wherein the rules are arranged as a decision tree.

5. The method of claim 3 wherein a top-level decision automatically identifies a cross-section having a relevant presence of plaque, wherein the relevant presence of plaque is determined at least based upon a minimum plaque thickness or stenosis.

6. The method of claim 1 wherein the classification criterion includes a rule based upon attachment of confluent dense calcium with confluent necrotic core.

7. The method of claim 1 wherein the classification criterion further includes a rule based on a percentage of fibro-fatty material present in a sample.

8. The method of claim 1 further comprising the step of rendering a graphical representation of a vessel segment displayed according to plaque classifications assigned to cross-sections of the vessel segment.

9. A computer-readable medium including computer-executable instructions facilitating classifying plaque within a vessel, the computer-executable instructions facilitating performing a set of steps comprising:

rendering a characterized tissue component map from a spectral analysis of ultrasound echo information for a vessel cross-section, wherein differing plaque components are distinguished, in the characterized tissue map, by assigned identifying values;

applying a classification criterion to spatially arranged data of the characterized tissue map, wherein the classification criterion includes a rule based upon a location, in relation to a lumen-plaque border, of confluent necrotic core within the vessel cross-section; and rendering, in response to the applying step, a plaque classification associated with the vessel cross-section.

10. The computer-readable medium of claim 9 wherein the plaque classification application applies a set of hierarchically arranged classification rules.

11. The computer-readable medium of claim 10 wherein the rules are arranged as a decision tree.

12. The computer-readable medium of claim 10 wherein a top-level decision automatically identifies a cross-section having a relevant presence of plaque, wherein the relevant presence of plaque is determined at least based upon a minimum plaque thickness or stenosis.

13. The computer-readable medium of claim 9 wherein the classification criterion renders a plaque classification for each vessel cross-section.

14. The computer-readable medium of claim 9 wherein the classification criterion includes a rule based upon attachment of confluent dense calcium with confluent necrotic core.

15. The computer-readable medium of claim 9 wherein the classification criterion further includes a rule based on a percentage of fibro-fatty material present in a sample.

16. The computer-readable medium of claim 9 further comprising the step of rendering a graphical representation of a vessel segment displayed according to plaque classifications assigned to cross-sections of the vessel segment.

17. A system for classifying plaque within a vessel, the system comprising:

a tissue characterization application for rendering a characterized tissue component map from a spectral analysis of ultrasound echo information for a vessel cross-section, wherein differing plaque components are distinguished, in the characterized tissue map, by assigned identifying values;

a plaque classification application for applying a classification criterion to spatially arranged data of the characterized tissue map, and rendering a plaque classification associated with the vessel cross-section, wherein the classification criterion includes a rule based upon a location, in relation to a lumen-plaque border, of confluent necrotic core within the vessel cross-section and wherein the classification criterion includes a rule based upon the presence of confluent necrotic core.

18. The system of claim 17 wherein the classification criterion renders a plaque classification for each vessel cross-section.

19. The system of claim 17 wherein the plaque classification application applies a set of hierarchically arranged classification rules.

20. The system of claim 19 wherein the rules are arranged as a decision tree.

21. The system of claim 19 wherein a top-level decision automatically identifies a cross-section having a relevant presence of plaque, wherein the relevant presence of plaque is determined at least based upon a minimum plaque thickness or stenosis.

22. The system of claim 17 wherein the classification criterion includes a rule based upon attachment of confluent dense calcium with confluent necrotic core.

23. The system of claim 17 wherein the classification criterion further includes a rule based on a percentage of fibro-fatty material present in a sample.

24. The system of claim 17 wherein the plaque classification application further comprises a graphical output processor that renders a graphical representation of a vessel segment displayed according to plaque classifications assigned to cross-sections of the vessel segment.

* * * * *